(12) United States Patent
Meyer

(10) Patent No.: US 9,072,704 B2
(45) Date of Patent: Jul. 7, 2015

(54) COMPOSITIONS AND METHODS FOR TREATMENT OF GLAUCOMA

(71) Applicant: Stellenbosch University, Stellenbosch, Western Cape Province (ZA)

(72) Inventor: David Meyer, Western Cape Province (ZA)

(73) Assignee: Stellenbosch University, Western Cape Province (ZA)

(*) Notice: Subject to any disclaimer, the term of this patent is extended or adjusted under 35 U.S.C. 154(b) by 0 days.

(21) Appl. No.: 14/044,004

(22) Filed: Oct. 2, 2013

(65) Prior Publication Data

US 2014/0045946 A1 Feb. 13, 2014

Related U.S. Application Data

(62) Division of application No. 12/672,475, filed as application No. PCT/IB2008/001979 on Jul. 30, 2008, now abandoned.

(30) Foreign Application Priority Data

Aug. 7, 2007 (ZA) .................. 2007/06585

(51) Int. Cl.
*A61K 31/167* (2006.01)
(52) U.S. Cl.
CPC .................. *A61K 31/167* (2013.01)
(58) Field of Classification Search
USPC .................. 514/630, 913
See application file for complete search history.

(56) References Cited

U.S. PATENT DOCUMENTS

| 5,270,050 A | 12/1993 | Coquelet et al. |
| 6,316,025 B1 | 11/2001 | Grattan |
| 2006/0074086 A1 | 4/2006 | Dolle et al. |

FOREIGN PATENT DOCUMENTS

| WO | WO-90/13290 | 11/1990 |
| WO | WO-01/08662 | 2/2001 |
| WO | WO-2004/050065 | 6/2004 |

OTHER PUBLICATIONS

PCT International Search Report in PCT/IB2008/001979, mailed Feb. 16, 2009, 6 pgs.
Van Der Bijl, P. et al., "Comparative Permeability of Human and Rabbit Corneas to Cyclosporin and Tritiated Water", *Journal of Ocular Pharmacology and Therapeutics* 2002, 18(5): 419-427.
Van Der Bijl, P. et al., "Comparative permeability of human vaginal and buccal mucosa to water", *European Journal of Oral Sciences* 1997, 105: 571-575.
Van Der Bijl, P. et al., "Diffusion rates of vasopressin through human vaginal and buccal mucosa", *European Journal of Oral Sciences* 1998, 106: 958-962.
Van Der Bijl, P. et al., "Effects of Three Penetration Enhancers on Transcorneal Permeation of Cyclosporine", *Cornea* 2001, 20 (5): 505-508.
Van Der Bijl, P. et al., "Permeation of Sumatriptan Through Human Vaginal and Buccal Mucosa", *Headache* Feb. 2000, 40: 137-141.
Bertolini, Alfio et al., "Paracetamol: New Vistas of an Old Drug", *CNS Drug Reviews*, vol. 12, No. 3-4 2006, 250-275.
Hogestatt, Edward et al., "Conversion of Acetaminophen to the Bioactive N-Acylphenolamine AM404 via Fatty Acid Amide Hydrolase-dependent Arachidonic Acid Conjugation in the Nervous System", *The Journal of Biological Chemistry*, vol. 280, No. 36 Sep. 9, 2005, 31405-31412.

*Primary Examiner* — Zohreh Fay
(74) *Attorney, Agent, or Firm* — Servilla Whitney LLC

(57) ABSTRACT

A new use for paracetamol in a method of treating glaucoma, which method comprises administering to a patient in need of such treatment 500 mg to 1000 mg of paracetamol in oral format 4 to 6 hourly. An ophthalmic solution is also provided containing between 0.1 to 5% of paracetamol which is administered as one to two drops in each eye 4 to 6 hourly. The ophthalmic solution further includes one or more of the following excipients: hydroxypropylmethylcellulose, benzalconium chloride, polyacrylic acid such as Teargel®.

4 Claims, 1 Drawing Sheet

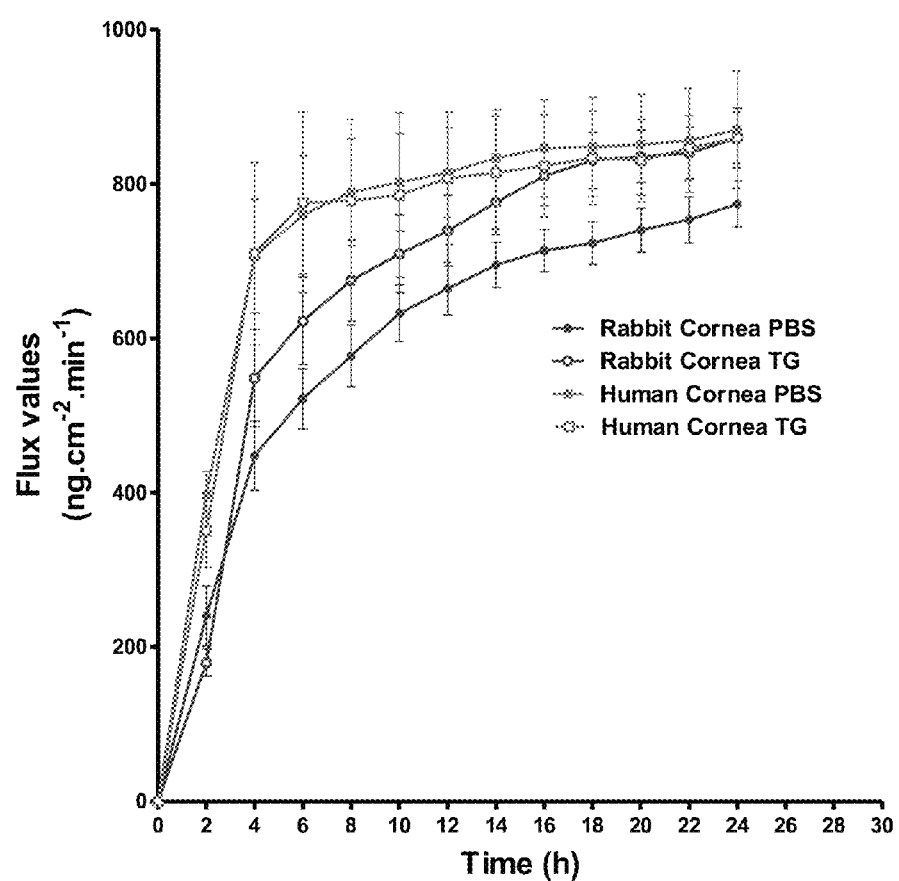

COMPOSITIONS AND METHODS FOR TREATMENT OF GLAUCOMA

CROSS-REFERENCE TO RELATED APPLICATIONS

This application is a divisional of U.S. application Ser. No. 12/672,475, filed Feb. 5, 2010, which is the national phase entry of International Application No. PCT/IB2008/001979, filed Jul. 30, 2008, which claims priority to South African Application No. 2007/06585, filed Aug. 7, 2007.

FIELD OF THE INVENTION

This invention relates to pharmaceutical compositions for use in the treatment of glaucoma and to methods of using such compositions.

BACKGROUND OF THE INVENTION

Glaucoma is a well-known eye disorder characterised by abnormally high pressure within the eyeball that leads to loss of retinal ganglion cells in a characteristic pattern of optic neuropathy. Although raised intraocular pressure is a significant risk factor for developing glaucoma, there is no set threshold for intraocular pressure that causes glaucoma. Nerve damage may occur at a relatively low pressure in some patients, while others may have high eye pressure for years and yet never develop damage. Glaucoma affects one in two hundred people aged fifty and younger, and one in ten over the age of eighty.

If not treated, however, glaucoma leads to permanent damage of the optic nerve and resultant visual field loss, causing impaired vision and sometimes blindness. The loss of visual field often occurs gradually over a long time and may only be recognized when it is already quite advanced.

Several drugs with different mechanisms of action are currently available for the treatment of glaucoma, each with a specific mechanism of action and efficacy or tolerability. New molecules and mechanisms of action are the subject of much research. Cannabis, or marijuana, is known to reduce the intraocular pressure. However, the widespread use of cannabis as an illegal recreational substance as well as its side effects have limited its application for treating the intraocular pressure in glaucoma.

SUMMARY OF THE INVENTION

It is an object of this invention to provide a medicament for use in the treatment of glaucoma.

In accordance with this invention there is provided paracetamol for use in a method of treating glaucoma, which method comprises administering to a patient in need of such treatment an effective amount of paracetamol (also known as acetaminophen).

According to one aspect of the invention there is provided for the paracetamol to be administered in the form of an ophthalmic solution; for the solution to contain between 0.1 to 5% of paracetamol; and for one to two drops of the solution to be administered to each eye 4 to 6 hourly.

According to a second aspect of the invention there is provided for the paracetamol to be administered to a patient in oral format 4 to 6 hourly.

The invention further provides an ophthalmic solution including as its active ingredient paracetamol.

Further features of the invention provide for the solution to include paracetamol in the range 0.1 to 5%; and for the solution to further include one or more of the following excipients: hydroxypropylmethylcellulose, benzalconium chloride, polyacrylic acid; and Teargel®.

The invention also provides for the use of paracetamol in the manufacture of a medicament for use in a method of treating glaucoma which method comprises administering to a patient in need of such treatment an effective amount of paracetamol.

The invention still further provides a method of treating glaucoma which includes administering to a patient in need thereof an effective amount of paracetamol.

Further features of the invention provide for the method to include the oral administration of paracetamol, alternately the ophthalmic administration of paracetamol to a patient.

The invention yet further provides a package which includes at least one dose of paracetamol in an amount effective for the treatment of glaucoma and instructions for the use thereof in a treatment for glaucoma.

Further features of the invention provide for the at least one dose to be suitable for oral administration, alternately suitable for ophthalmic administration.

BRIEF DESCRIPTION OF THE DRAWING

The FIGURE is a two-dimensional line graph showing mean flux values of paracetamol in aqueous solution (0.1%) and Teargel® (0.1%) across human and rabbit corneas where bars represent the standard error of the mean.

DETAILED DESCRIPTION OF THE INVENTION

Treatment of Patients with Glaucoma

In initial trials, 1000 mg of paracetamol was administered orally 4 to 6 hourly to several patients with glaucoma. In all cases the intra-ocular pressure reduction was in the order of 30% after 24 to 48 hours. This compares well with the pressure lowering effect of currently available commercial preparations.

Extrapolating from this test, it appears that a dosage in the range of 500 to 1000 mg should be sufficient to treat glaucoma. Whilst such doses every 4 to 6 hours have been shown to be effective, it is possible that this frequency could be reduced.

Although the mechanism of action in the present application is not fully understood it is suspected that it is through paracetamol's indirect activation of cannabinoid CB1 receptors. The CB1 receptor is expressed in the central nervous system, eye and numerous other tissues and has been recognized as an important therapeutic target for glaucoma. It is suspected that it is through this pathway that paracetamol acts to reduce intra-ocular pressure.

Given the effects of paracetamol on the hepatic and renal systems, an ophthalmic solution was proposed as the preferable manner of delivering an effective amount of paracetamol to the eye in a glaucoma patient.

An ophthalmic solution was made up as follows: 1 mg/ml (0.1%) solution of paracetamol in phosphate buffered saline (pH=7.4) was used for half of the experiments and 1 mg/ml (0.1%) solution of paracetamol in phosphate buffered acrylic acid suspension was used for the experiments on rabbit corneas. In more than 2000 corneal penetration experiments it has been demonstrated that paracetamol does penetrate the cornea well. Corneal penetration is statistically significantly improved when the paracetamol is suspended in polyacrylic acid gel. These tests were conducted in the following manner.

Materials and Methods
Cornea Specimens

Harvested donor corneas, which were deemed unsuitable for transplantation because of infections such as hepatitis B and human immunodeficiency virus (HIV), were obtained from The Eye Bank Foundation of South Africa Observatory from 6 patients (mean age±SD, 35±12 years; range, 24-65 years). In addition, rabbit corneas were obtained from 6 freshly slaughtered rabbits (Country Lane Nursery Farm, Kraaifontein, Cape Town, South Africa). Excised corneas were immediately placed in McCarey-Kaufman solution and transported to a laboratory within 6 hours. The McCarey-Kaufman solution consisted of a stock solution of Medium 199 (Sigma Chemical Company, St. Louis, Mo., U.S.A.) to which sodium bicarbonate, as well as 25 mM of HEPES and 5% dextran, was added before using the solution for the transport of corneal specimens. On arrival in the laboratory, the corneas were hemisected. One half was used immediately, and the other half was snap-frozen in liquid nitrogen and stored at −85° C. for no longer than 6 months before use. At least one piece of corneal tissue from each specimen was placed in formalin and retained for histologic examination.

No specimens were obtained in which there was clinical evidence of any corneal disease or pathology that might have influenced the permeability characteristics of the cornea. The study was approved by the Ethics Committee of the Faculty of Health Sciences, University of Stellenbosch and the Tygerberg Academic Hospital in Cape Town, South Africa.

Permeability Experiments and Histology

Before each permeability experiment, tissue specimens were thawed at room temperature in phosphate buffered saline (PBS, pH 7.4). Although some damage may have occurred on a cellular level, the processes of freezing, storage, and thawing were demonstrated to have no adverse effects on the permeability characteristics of corneal tissues in 2 previous studies (Van der Bijl et al., 2001; Van der Bijl et al., 2002). Thereafter, corneas were very carefully cut, so as not to damage either the endo- or epithelial surfaces, into 4-mm$^2$ sections and mounted in flow-through diffusion cells (exposed areas, 0.039 cm2) as previously described (Van der Bijl et al., 1997; Van der Bijl et al., 1998; Van der Bijl et al., 2000). Each experiment using the paracetamol solution was repeated six times for the human and rabbit corneas, respectively. Before commencing each permeability experiment, tissue disks were equilibrated for 10 minutes with PBS (pH 7.4) at 20° C. in both the donor and receiver compartments of the diffusion cells.

Following equilibration, the PBS was removed from the donor compartment and replaced with 1.0 mL of PBS, containing 1 mg/mL (0.1%) paracetamol in PBS at pH 7.4 (w/v) or else 1 mg/mL (0.1%) paracetamol in a commercially available artificial tear gel i.e. Teargel® liquid gel (Restan Laboratories, Bryanston, South Africa). The latter is a highly viscous clear gel, with an extended tear film break-up time. The gel, after its addition to the donor chamber, was capped completely with a tight-fitting teflon disc and 1 mL of PBS deposited on top of the disc. The PBS did not, in any way, mix with the gel, but was simply used to prevent dessication of the gel during the 24-hour experiment. Each gram of the latter gel contains 2 mg of polyacrylic acid and cetrimide 0.01% m/m as a preservative. PBS at 20° C. was pumped through the receiving chambers at a rate of 1.5 ml/h with a ISMATEC® 16 Channel High precision tubing pump and collected, by means of a ISCO Retriever IV fraction collector, at 2-h intervals for 24 h. The permeability studies were performed under sink conditions, i.e. at the completion of each run the concentration of paracetamol solution in the acceptor chamber never reached 10% of that in the donor compartment. Paracetamol containing samples were collected in appropriate sampling tubes of the fraction collector. Samples were analyzed at the Division of Pharmacology, Faculty of Health Sciences, Stellenbosch University by HPLC with UV detection. The collected fractions were analyzed directly after completion of the respective experiment for their paracetamol content.

Calculation of Flux Values

Flux (J) values across membranes were calculated by means of the relationship $$J = Q/A \times t \; (\text{ng} \times \text{cm}^{-2} \times \text{min}^{-1})$$

where Q indicates quantity of substance crossing membrane (in ng); A, membrane area exposed (in cm$^2$); and t, time of exposure (in minutes).

Steady State Kinetics

When no statistically significant differences (p<0.05; analysis of variance and Duncan's multiple range test) between flux values were obtained over at least two consecutive time intervals, a steady state (equilibrium kinetics) was assumed to have been reached for a particular corneal specimen.

Statistical Analysis

Non-linear regression analyses (third order polynomials) were performed using a GraphPad Prism, Version 4, 2003 computer programme. An F test was used to compare entire curves. A t-test at steady state, was also performed for comparative purposes. A significance level of 5% was used for all tests and comparisons.

HPLC Detection of Paracetamol

Permeant-containing effluent samples, collected from the acceptor compartments of the perfusion apparatus over the 2-hour sampling intervals, were analyzed using an Hewlett Packard 1100 series high-performance binary liquid chromatograph (Agilent Technologies, Waldbronn, Germany) equipped with an Agilent Eclipse (XDB-C18) Zorbax analytical column (3.5-µm particle size), 150×4.6 mm (ID). The latter column was preceded by a 30×2.1-mm (ID) C18 guard column (40-µm particle size). The temperature was maintained at 40° C. and a flow rate of 1.0 mUmin was used for the entire run. The mobile phase consisted of a mixture of 2 solvents, A (50 mol/L KH$_2$PO$_4$, pH 5.4) and B (acetonitrile-isopropanol, 4:1 vol/vol). Three isocratic mixtures of A:B were used in sequential order as follows: firstly for 0 to 1.0 min: 90% Solvent A/10% Solvent B; secondly for 1 to 4.0 min: Linear gradient to 70% Solvent A/30% Solvent B, thirdly for 4.10 mins: return to use of 90% Solvent A/10% Solvent B. An equilibration time of 2.5 min was used for 90% Solvent A/30% Solvent B. All reagents used for the mobile phase were HPLC grade (Burdick & Jackson, Honeywell International Inc, Muskegon, Mich.), and all inorganic solvents were filtered through a 0.45-µm filter. Deionized water was used for preparing all aqueous standard and buffer solutions. Aliquots (15 µL) from each fraction sample were injected directly onto the column. Since no extraction procedure was required, it was unnecessary to determine recovery rates. Paracetamol was detected at 245 nm (retention time, 3.45 mins), while the total run time was set at 5.0 minutes. Recording and integration of peaks were performed by means of an Agilent Chem Station. Spiked standards over the expected concentration range of 250 ng/ml to 4000 ng/ml (4.0 µg/ml) were randomly included in each batch on a variable wave Detector (Agilent, Waldbonn, Germany). Calibration was linear over the entire concentration range (R$^2$=0.9999).

Results

Permeability Experiments

Mean flux values for 0.1% paracetamol in aqueous solution (PBS) and Teargel (TG) across the frozen/thawed rabbit and human cornea versus time are shown in FIG. 1. The diffusion rates of paracetamol (in both PBS and TG) across human corneas were higher in the first few hours of the diffusion experiment than the values found across rabbit corneas. Steady state was also reached much earlier for paracetamol diffusion across human corneas. Teargel as a soluent did not affect the diffusion rate of paracetamol across human corneas as the graphs are nearly identical. Teargel does, however, increase the diffusion rate of paracetamol across rabbit corneas.

Statistically significant differences (P<0.05) were obtained when whole curves are compared using an F-test ($3^{rd}$ degree polynomial) between the steady-state flux values of: paracetamol (TG) and paracetamol (in PBS) across rabbit corneas (P<0.0001); paracetamol (in PBS) across rabbit and human corneas (P<0.0001); and paracetamol (TG) across rabbit and human corneas (P=0.0095). No statistically significant differences were found for paracetamol (TG) and paracetamol (in PBS) across human corneas (P=0.9939).

For paracetamol from 0.1% paracetamol in PBS, steady-state flux values were 774±30 $ng \cdot cm^{-2} \cdot min^{-1}$ and 870±76 $ng \cdot cm^{-2} \cdot min^{-1}$ across rabbit and human cornea respectively (FIG. 1). For paracetamol from 0.1% paracetamol in TG, steady-state flux values were 860±39 $ng \cdot cm \cdot min^{-1}$ and 860±33 $ng \cdot cm^{-2} \cdot min^{-1}$ across rabbit and human cornea respectively (FIG. 1).

CONCLUSIONS

As paracetamol has been safely used in humans for more than 100 years and its effects on the body are well known, the invention provides a promising breakthrough in the treatment of glaucoma. This is particularly so for paracetamol in an ophthalmic solution which shows good corneal permeability of paracetamol. This has the benefits of the paracetamol acting directly on to have a direct effect on the therapeutic targets for glaucoma as well as reducing its effects on the hepatic and renal systems.

It is envisaged that doses of paracetamol which are effective in the treatment of glaucoma will be packaged together with instructions for the use thereof in the treatment of this condition. Such doses could be intended for oral administration and could consist of one or more tablets, capsules or the like. Alternately the doses could be intended for ophthalmic administration and could be provided by one or more containers of a suitable ophthalmic solution intended for single or repeated use.

It will be appreciated that many other embodiments of the invention exist which fall within the scope of the invention, particularly as regards dosage forms and therapeutic regimens.

What is claimed is:

1. A method for treating glaucoma comprising administering paracetamol ophthalmically to a patient with glaucoma in an amount effective to treat the glaucoma.

2. The method of claim 1 wherein the paracetamol is administered in the form of an ophthalmic solution or gel.

3. The method of claim 2 wherein the ophthalmic solution or gel contains between about 0.1 and 5% of paracetamol.

4. The method of claim 2 wherein the paracetamol is administered as one to two drops of the solution to each eye 4 to 6 hourly.

* * * * *